United States Patent
Ritz

[19]

[11] Patent Number: 5,976,183
[45] Date of Patent: Nov. 2, 1999

[54] SEWING RING FOR HEART VALVE PROSTHESIS

[75] Inventor: Joseph P. Ritz, Austin, Tex.

[73] Assignee: Medical Carbon Research Institute, LLC, Austin, Tex.

[21] Appl. No.: 09/002,654

[22] Filed: Jan. 5, 1998

[51] Int. Cl.$^6$ ...................................................... A61F 2/24
[52] U.S. Cl. .................................................................. 623/2
[58] Field of Search ........................................ 623/2, 900

[56] References Cited

U.S. PATENT DOCUMENTS

| | | |
|---|---|---|
| 3,365,728 | 1/1968 | Edwards et al. . |
| 3,371,352 | 3/1968 | Siposs et al. . |
| 4,535,483 | 8/1985 | Klawitter et al. ............................ 623/2 |
| 5,032,128 | 7/1991 | Alonso ........................................ 623/2 |
| 5,035,709 | 7/1991 | Wieting et al. .............................. 623/2 |
| 5,071,431 | 12/1991 | Sauter et al. ................................ 623/2 |
| 5,104,406 | 4/1992 | Curcio et al. ................................ 623/2 |
| 5,397,346 | 3/1995 | Walker et al. ............................... 623/2 |
| 5,607,470 | 3/1997 | Milo ............................................ 623/2 |
| 5,766,240 | 6/1998 | Johnson ...................................... 623/2 |

Primary Examiner—David H. Willse
Attorney, Agent, or Firm—Fitch, Even, Tabin & Flannery

[57] ABSTRACT

A sewing ring for a heart valve prosthesis to allow the valve to be sutured into operative position in association with a region of a human heart from which a defective valve has been excised. The generally cylindrical exterior surface of a valve body of circular cross-section is provided with either an encircling groove or a protruding annular band. To interconnect with such groove or band, a metal split sleeve is provided which has either a radially inward directed projection or an annular cavity for mating, respectively, with the groove or band of the valve body. A tubular fabric sleeve from which a sewing cuff is constructed is first fitted about the valve body, and a central portion of such fabric sleeve is sandwiched between the split sleeve and the valve body so that it is entrapped and preferably compressed between the interconnecting elements. A continuous locking ring, e.g. a rigid tubular metal sleeve, is frictionally fit about the exterior surface of the split sleeve to lock the fabric sleeve in place, which is then fashioned into a sewing cuff. The components may be sized so that the cuff is rotatable on the valve body or non-rotatable, as desired.

18 Claims, 2 Drawing Sheets

SEWING RING FOR HEART VALVE PROSTHESIS

FIELD OF THE INVENTION

The present invention relates to heart valve prostheses having sewing rings to facilitate implantation and more particularly to improved arrangements for mounting sewing rings exterior of a valve body to facilitate fabrication and assembly of a prosthetic heart valve.

BACKGROUND OF THE INVENTION

A wide variety of mechanical heart valves have been developed for the replacement of defective natural valves. Artificial valves are essentially check valves that operate hemodynamically and in conjunction with the pumping action of the heart. These valves commonly have a valve body of generally hollow cylindrical shape which is designed to support one, two or three occluders or leaflets that are arranged to alternately open and close in order to permit or halt blood flow through a central passageway therein. To install such prosthetic valves into a location associated with a human heart from which a defective natural valve has been excised, a sewing ring is commonly provided which surrounds the valve body and which includes a generally annular cuff through which the prosthetic valve assembly can be sutured to the surrounding tissue to implant the valve in its desired location. Examples of such sewing rings are shown in U.S. Pat. Nos. 4,535,483, 5,035,709 and 5,104,406.

Conventional sewing rings often are fabricated from tubes or sleeves of cloth made of Dacron™ fabric or the like. Such a sleeve is often appropriately tied in place by cords or held in place by a plurality of rings, frequently in conjunction with a metal stiffening ring that will be shrink-fit onto the exterior of the valve body when a pyrocarbon valve body is employed. The tubular cloth sleeve is then often rolled upon itself, and its ends may be individually secured or stitched in some way to each other to complete the assembly. Often a foam material ring is incorporated within the rolled tube to serve as a filler that can be easily penetrated by suturing needles.

Just as improvements continue to be sought in the design of occluder constructions for prosthetic heart valves, improvements are likewise sought for heart valve sewing rings, including improvements which will simplify the assembly of such sewing rings and thus reduce the production expense.

SUMMARY OF THE INVENTION

Generally, the present invention provides a sewing ring assembly for a prosthetic heart valve, particularly one having a pyrocarbon valve body, which securely attaches a tubular fabric sleeve to such a body and effectively installs a stiffening ring without the need for shrink-fitting. The sewing ring arrangement employs split sleeve means which is formed with interconnecting means to interengage with complementary means on the exterior surface of the valve body so as to prevent disengagement in an axial direction, in combination with locking means which encircles the split sleeve means and becomes frictionally engaged thereabout. As a result of this encirclement and frictional engagement, the split sleeve becomes mounted upon the valve body as a stiffening ring and simultaneously secures the tubular cloth sleeve in place, sandwiching it against the exterior of the valve body. The locking means is sized so that the sewing ring is rotatable or non-rotatable as desired.

In a preferred embodiment, the tubular fabric sleeve is first installed over the otherwise completed valve so that it preferably extends past both the upstream and the downstream ends of the valve body. A split metal sleeve having interconnecting means in the form of an annular cavity or groove in its interior surface that is proportioned to receive a protruding band on the exterior of the valve body is then installed over the fabric sleeve sandwiching it against the surface of the valve body. Alternatively, the split sleeve may be formed with a central protrusion that extends radially inward and is received in interconnecting means in the form of a groove in the outer surface of the valve body. Locking means of the continuous ring type, for example a metal tube having an interior diameter proportioned so as to frictionally engage at least a portion of the outer surface of the split sleeve, is then installed so as to encircle and lock the split sleeve in place upon the valve body. The inner diameter of the locking tube will determine whether the sewing cuff is rotatable. Thereafter, the ends of the tubular fabric sleeve are suitably rolled and/or secured to each other to complete the fabrication of the sewing ring that encircles the valve body. Instead of using a tubular locking sleeve, one or more continuous rings of metal or other suitable material may be installed to encircle the split sleeve and lock it in place on the heart valve body.

DETAILED DESCRIPTION OF THE PREFERRED EMBODIMENTS

Figure 1:
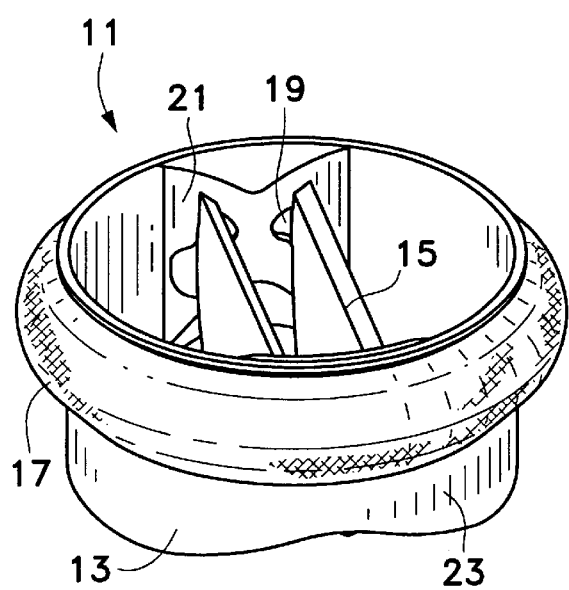
FIG. 1 is a perspective view of a bi-leaflet heart valve having a sewing ring installed thereon which embodies various features of the present invention.

Illustrated in FIG. 1 is a heart valve 11 which includes a valve body 13 in which a pair of occluders or leaflets 15 are mounted and which carries an encircling sewing ring 17 for suturing the heart valve in place. The occluders 15 are supported for general pivoting movement between an open position which allows blood flow therethrough in a downstream direction (which in the orientation in FIGS. 1, 3 and 4 would be vertically downward) and a closed position which prevents significant flow in the opposite upstream direction. The leaflets 15 are guided in their movement by pairs of shaped cavities 19 that are formed in flat wall sections 21 of the interior surface of the valve body, which cavities receive ears (not shown) that are integral parts of the leaflets and extend laterally therefrom. The details of the valve operating mechanism form no part of the present invention, being the subject matter of U.S. Pat. No. 5,545,216, the disclosure of which is incorporated herein by reference.

The valve body 13 has a flared entrance 25 and an exterior surface 23 which is generally cylindrical except for a central band or protrusion 27 which projects radially outward. The band 27 has a rectilinear outer surface which is a section of a circular cylinder, and it has upstream and downstream generally transverse annular surfaces 29, 31. The valve body may be made from any suitable material, and preferred materials include pyrocarbon and pyrocarbon-coated graphite substrate in which case the protruding band is part of a unitary structure with the remainder of the valve body.

Figure 2:
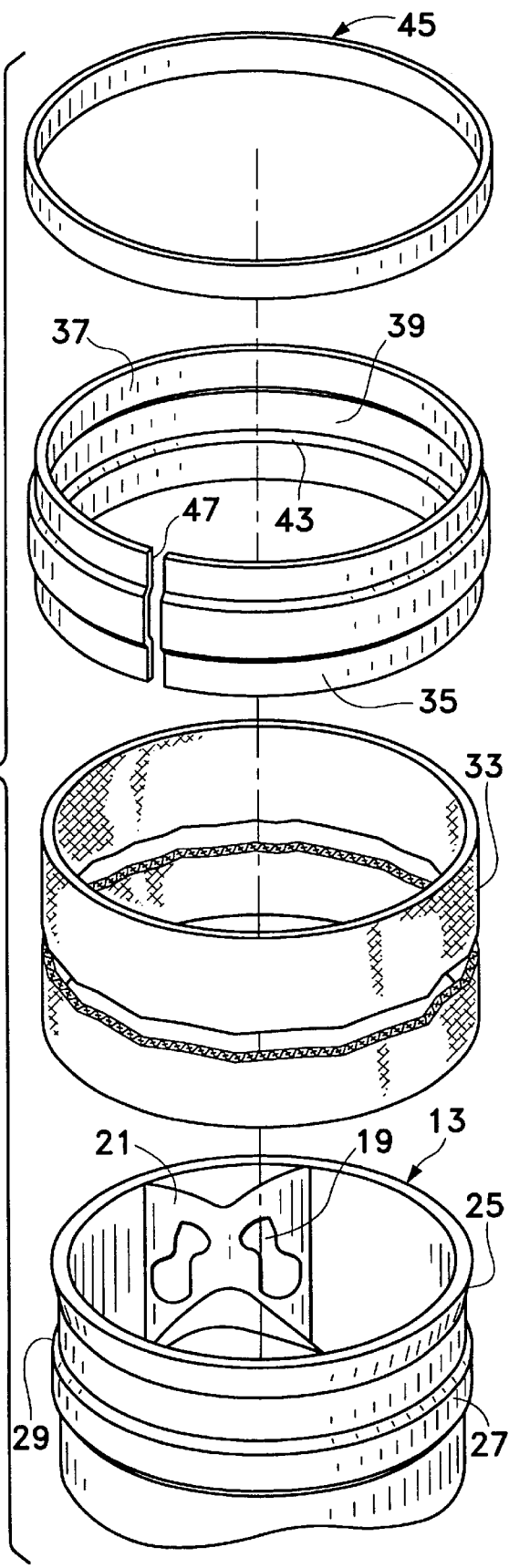
FIG. 2 is an exploded perspective view showing the heart valve of FIG. 1 and the individual elements of the sewing ring assembly, with the valve leaflets omitted from the valve body and the tubular sleeve broken away centrally to foreshorten it.

The sewing ring 17 is formed using a seamless tubular fabric or cloth sleeve 33 which may be of woven or knitted fabric made from polyester or PTFE fibers, selected for lifetime durability as well as overall compatible with blood and with heart tissue. The fabric tube may be optionally coated with vapor-deposited carbon, such as that marketed under the trademark Biolite, which gives the exposed fabric surface high thromboresistance. The fabric sleeve 33 has a substantial axial length (being shown foreshortened in FIG. 2) and may commonly have an overall length from about one to about four times the length of the valve body 13, depending upon the particular construction of the sewing cuff that is employed. The sleeve is proportioned to fit over the valve body in encircling relationship, as shown in FIG. 3, and to extend beyond both the upstream and the downstream ends of the valve body.

To secure the fabric tube portion of the sewing ring in place, a split ring or sleeve 35 is used which is shaped to complement the exterior shape of the valve body 13. The split sleeve 35 is made of a suitable material, preferably a metal such as titanium, e.g. titanium 6AL-4V, which is biocompatible; it also may be made from stainless steel or alloys of chromium and cobalt. The illustrated split sleeve 35 has an interior cylindrical surface 37 which is formed with a central cavity 39 that is shaped to match the shape of the band 27 that encircles the exterior of the valve body 13, which cavity accordingly has a pair of upstream and downstream generally transverse walls 41, 43 that are complementary to the annular surfaces 29, 31 as can be seen from the assembled view of FIG. 3. It has a gap between its facing ends 47.

In the assembly, the fabric sleeve 33 is sandwiched between the exterior surface of the valve body and the interior surface of the split sleeve 35. The split sleeve can be opened to easily be installed over the tubular sleeve, and then when compressed to a smaller diameter so the free ends 47 of the split ring abut or nearly abut, as desired, it will tightly squeeze the fabric sleeve in this sandwich arrangement, securing the fabric sleeve 33 to the valve body. A continuous locking sleeve or ring means 45 is then installed, being inserted over the upstream end of the valve body in sliding contact with the upper region of the exterior surface of the split ring as shown in FIG. 3. The locking sleeve 45 is sized so as to have a light interference fit against the outer surface of the split sleeve 35 so there is frictional engagement therebetween. The proportioning is such that the thickness of the band plus the thickness of the fabric serves to lock the split sleeve 35 in place about the band 27 on the valve body. With the split sleeve 35 locked in place, the fabric sleeve 33 is likewise squeezed and locked between the band 27 and the walls of the cavity 39 so it likewise will not move either upstream or downstream. The locking sleeve 45 is preferably sized with respect to its interior diameter so that the cuff fabric material will still slide about the valve body surface so as to allow rotation by application of a torque of about 20 inch-ounces or less. However, if desired, by use of locking sleeve 45 of slightly smaller diameter, the frictional engagement can be increased to render the sewing ring non-rotatable. If desired, a second optional locking sleeve (see FIG. 3A, sleeve 49) could be installed to encircle the downstream portion of the split sleeve 35 below the region where the cavity 39 is formed.

Figure 3A:
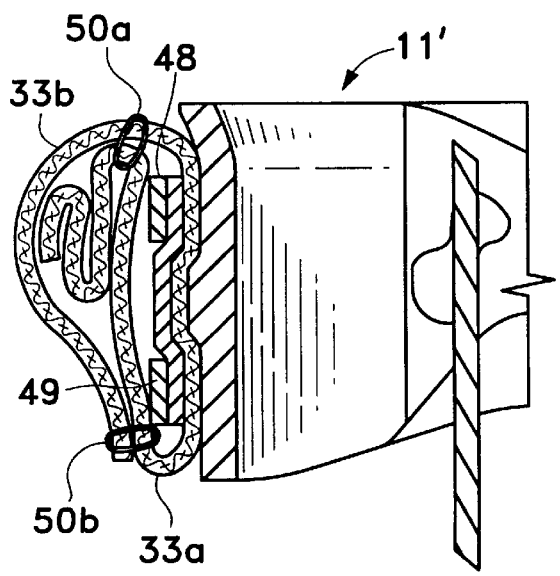
FIG. 3A is a fragmentary sectional view similar to FIG. 3 showing the sewing ring assembly, which incorporates a second locking sleeve, which is completed to illustrate a suitable sewing cuff construction.
Figure 3:
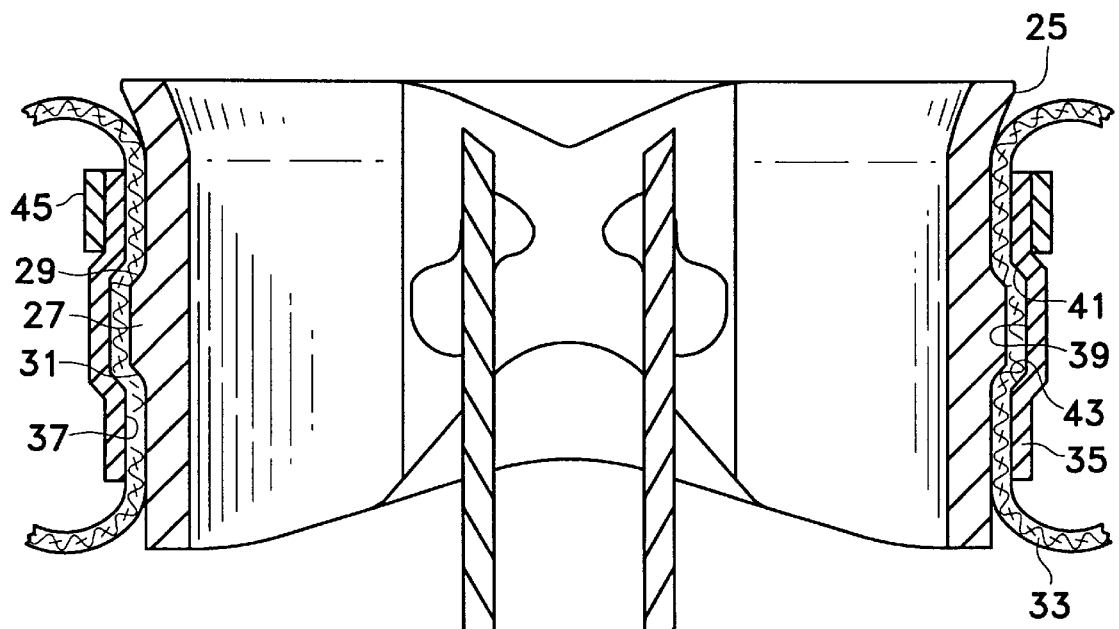
FIG. 3 is a sectional view of a partial assembly of the heart valve of FIG. 1 showing the interengagement of the various components shown in FIG. 2 as installed on the valve body.

Once the fabric sleeve 33 is locked in place, the cuff portion of the sewing ring is constructed by suitably folding or rolling the respective ends of the fabric sleeve, the beginning of such fabrication being depicted in FIG. 3. For example, the upstream end portion of the sleeve 33 may be folded over onto itself to create a plurality of material thicknesses suitable to function as a sewing cuff before the ends are either appropriately stitched to each other or appropriately tied off with ties as well known in the art in order to create an annular cuff of the type illustrated in FIG. 1, or a cuff might be constructed as illustrated in FIG. 3A. If desired, a filler ring of pliable plastic material, such as a fluorosilicone rubber or a similar synthetic polymeric material which, although pliable, will retain a molded shape and which is sterilizable, biologically inert and nontoxic to body fluids and tissues. The use of such filler rings and tie cords and, optionally, additional metal locking rings is described in detail in U.S. Pat. No. 5,178,633, the disclosure of which is incorporated herein by reference.

FIG. 3A illustrates a heart valve 11' which is the same as the valve 11 except that a second locking sleeve 49 is installed on the downstream half of the split sleeve so that the exterior surface of the split sleeve is frictionally engaged both upstream and downstream of the region where the cavity lies. In addition, FIG. 3A illustrates one typical folding arrangement which might be used to create an annular sewing cuff from the upstream portion of the tubular fabric sleeve 33. In the illustrated arrangement, the downstream section 33a is folded upward and then joined to the upstream section 33b with a baste stitch 50a; it is then folded several times upon itself. After such folding is accomplished, the end of the upstream section 33b of the fabric sleeve 33 is folded downward about the assembly and stitched at 50b to the section 33a to complete the cuff. If desired, one or more ties as well known in this art can be used to secure the configuration of the cuff. As mentioned above, a soft polymeric filler could, if desired, be included within the sewing cuff to cause it to retain a more specific shape.

Figure 4:
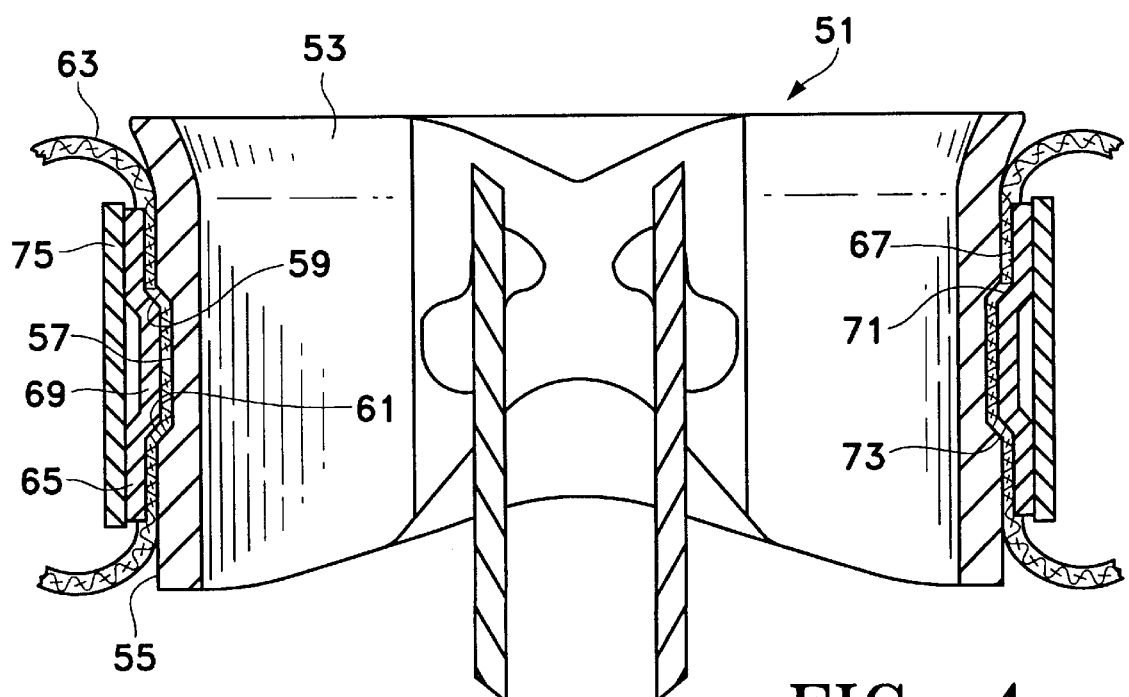
FIG. 4 is a sectional view similar to FIG. 3 of an alternative embodiment of a sewing ring arrangement embodying various features of the invention.

Illustrated in FIG. 4 is an alternative version of a heart valve 51 having a valve body 53, the interior of which is the same as the valve body 13. However, its exterior surface 55 is generally cylindrical except for a groove 57 which encircles the entire body and constitutes a cylindrical base wall of a diameter less than that of the exterior surface 55. Flanking the base wall are a pair of generally transverse surfaces 59 and 61 which are annular transition surfaces between the rectilinear base wall and the exterior cylindrical surface 55.

A tubular fabric sleeve 63, the same as the sleeve 33 described hereinbefore, is installed in surrounding relationship about the valve body 53, and then a split sleeve 65 is installed over it. The split sleeve 65 has an interior cylindrical surface 67 proportioned to lie in juxtaposition with the exterior surface 55 of the valve body, and it contains a central projection 69 which extends radially inward and is proportioned to be received in and substantially fill the groove 57 with the fabric sleeve 63 sandwiched therebetween. The interior projection 69 has upstream and downstream annular surfaces 71, 73 which are generally transverse to the cylindrical surface 67 and are complementary to the annular transverse surfaces 59, 61 of the groove.

With the split sleeve 65 in place, a locking sleeve 75 is installed which has an axial length just slightly longer than that of the split sleeve. In the initially installed condition, the slot adjacent the two free ends of the split sleeve 65 will be open; however, the gap will close or nearly close when the locking sleeve 75 is pressed into position. There should be at least a slight interference fit between the two sleeves so there will be good frictional engagement between the interior surface of the locking sleeve 75 and the exterior surface of the split sleeve 65. In this condition, the tubular fabric sleeve 63 is locked in place between the juxtaposed walls of the projection 69 and the groove 57 and will not move axially. The upstream and downstream ends of the fabric sleeve 63 are then manipulated, as hereinbefore described, to create a sewing cuff.

Although the invention has been described in terms of the preferred embodiments which constitute the best mode presently known for carrying out the invention, it should be understood that various changes and modifications as would be obvious to those having ordinary skill in this art may be made without departing from the scope of the invention which is defined in the appended claims. For example, if desired, instead of having a unitary valve body wherein a cylindrical band protrudes outward therefrom, a stiffening ring could be affixed frictionally to or shrink-fit onto the exterior surface of a valve body having an essentially cylindrical external surface. Although the band 27 is continuous in its encirclement of the valve body, if desired, the band could be interrupted at a plurality of locations without significantly altering the interconnection between the outwardly protruding band 27 and the cavity in the split ring 35. Instead of using a locking sleeve 45 or 75 or a pair of sleeves 45, 49, upper and lower continuous locking rings could be used. Such unitary rings could be of circular, rectangular, e.g. square, triangular, oval, or any suitable cross-section, so long as they are sized to frictionally engage in interference fit with the exterior surface of the split sleeve; one such ring would preferably be installed upstream of the cavity region 39 on the sleeve 35 and the other ring installed downstream thereof as in the case of the locking sleeves 45, 49. Although the sewing ring is illustrated with a bileaflet heart valve, it could be installed as a part of a trileaflet or a single occluder heart valve.

Various features of the invention are emphasized in the claims which follow.

What is claimed is:

1. A heart valve prosthesis which comprises:

a valve body of generally circular cross-section having an exterior surface and including means for allowing flow therethrough in a downstream direction and preventing significant flow in an opposite upstream direction, and a sewing ring carried by said valve body exterior surface for installing the prosthesis in association with a human heart, said valve body exterior surface being formed with first interconnecting means that generally encircles said valve body, and said sewing ring including (a) split sleeve means having second interconnecting means that interengages with said first interconnecting means when installed in surrounding relationship about said valve body and that, when so interengaged, prevents relative upstream-downstream movement therebetween, said split sleeve means having two free ends, (b) tubular cloth sleeve means sandwiched between said valve body exterior surface and said split sleeve means in the region of said first and second interconnecting means and being of such a length so as to extend beyond upstream and downstream ends of said split sleeve means, and (c) rigid circular continuous locking means that is slidable onto and fitted peripherally about said split sleeve means in frictional engagement thereabout so as to lock said cloth sleeve means between said first and second interconnecting means by frictional engagement between said valve body exterior surface and said split sleeve means and prevent disengagement therebetween, whereby said tubular cloth sleeve means is securely attached to said valve body for formation of a sewing cuff for suturing said prosthesis to tissue associated with a human heart.

2. The prosthesis according to claim 1 wherein opposite ends of said tubular cloth sleeve means are folded over and cover the entire exterior surface of said split sleeve means and said continuous locking means, with at least one said end being secured to complete the exterior surface of said sewing cuff.

3. The prosthesis according to claim 1 wherein said first interconnecting means comprises groove means in said exterior surface of said valve body that is otherwise generally cylindrical and wherein said second interconnecting means comprises interior projection means extending radially inward from an otherwise cylindrical surface of said split sleeve means, which interior projection means is proportioned to be received in and substantially fill said groove means with said cloth sleeve sandwiched therebetween.

4. The prosthesis according to claim 3 wherein said groove means has upstream and downstream interior surface sections which are aligned generally transverse to said exterior surface of said valve body and wherein said projection means sandwiches said tubular cloth sleeve means frictionally against said upstream and downstream interior surface sections in said groove means.

5. The prosthesis according to claim 1 wherein said continuous locking means encircles said split sleeve means so that said free ends are spaced apart to provide a gap therebetween.

6. The prosthesis according to claim 5 wherein the inner diameter of said circular locking means is proportioned so that said sewing cuff is rotatable upon said valve body with a torque of about 20 inch-ounces or less.

7. The prosthesis according to claim 5 wherein said continuous locking means is a rigid tubular sleeve.

8. The prosthesis according to claim 7 wherein said encircling tubular sleeve has an upstream-downstream length about equal to the upstream-downstream length of said split sleeve means.

9. The prosthesis according to claim 1 wherein said valve body first interconnecting means includes radially outwardly extending protrusion means and wherein said split-sleeve means has an interior surface proportioned to lie in juxtaposition with said exterior surface of said valve body with said second interconnecting means including cavity means formed in said interior surface of said split sleeve means, said cavity means being proportioned to fit about and closely accommodate said outward protrusion means with said tubular cloth sleeve means sandwiched therebetween.

10. The prosthesis according to claim 9 wherein said cavity means has upstream and downstream surface sections aligned generally transverse to said interior surface and wherein said protrusion means has complementary surfaces whereby said tubular cloth sleeve means becomes frictionally sandwiched between said upstream and downstream interior surface sections in said cavity means and said complementary surfaces.

11. The prosthesis according to claim 10 wherein said circular continuous locking means encircles said split sleeve means so that said free ends are spaced apart to provide a gap therebetween.

12. The prosthesis according to claim 11 wherein said continuous locking means is a rigid tubular sleeve.

13. The prosthesis according to claim 12 wherein said encircling tubular sleeve has an upstream-downstream length such that it extends along an exterior surface of said split sleeve means from the region of said cavity means to about the adjacent upstream or downstream end of said split sleeve means.

14. A heart valve prosthesis which comprises:
   a valve body of generally circular cross-section which includes means for allowing flow therethrough in a downstream direction and preventing significant flow in an opposite upstream direction, and
   a sewing ring carried by said valve body for installing the prosthesis in association with a human heart,
   said valve body having an exterior surface which is formed with first interconnecting means that generally encircles said valve body, and
   said sewing ring including
      (a) tubular fabric sleeve means in surrounding relationship to said valve body for formation into annular cuff means through which said prosthesis can be sutured to tissue associated with a human heart,
      (b) split sleeve means that encircles said fabric sleeve means, which has two free ends and has second interconnecting means that interengages with said first interconnecting means when installed in surrounding relationship about said valve body and that, when so interengaged, prevents relative upstream-downstream movement therebetween, and
      (c) rigid circular continuous locking means that is slidable onto and encircles said split sleeve means in frictional engagement thereabout so as to lock said first and second interconnecting means in engagement with each other with said fabric sleeve means sandwiched therebetween in frictional engagement between said valve body exterior surface and said split sleeve means so as to prevent disengagement therebetween.

15. The prosthesis according to claim 14 wherein said first interconnecting means comprises groove means in a cylindrical exterior surface of said valve body and wherein said second interconnecting means comprises interior projection means extending radially inward from an otherwise cylindrical surface of said split sleeve means, which interior projection means is proportioned to be received in and substantially fill said groove means.

16. The prosthesis according to claim 14 wherein said first interconnecting means includes radially outwardly extending protrusion means, wherein said second interconnecting means includes cavity means formed in an interior surface of said split sleeve means for fitting about and closely accommodating said protrusion means, and wherein said tubular fabric sleeve means is sandwiched between said protrusion means and said cavity means.

17. A heart valve prosthesis which comprises:
   a valve body of generally circular cross-section which includes means for allowing flow therethrough in a downstream direction and preventing significant flow in an opposite upstream direction, and
   a sewing ring carried by said valve body for installing the prosthesis in association with a human heart,
   said valve body having a generally cylindrical exterior surface which is formed with first interconnecting means that generally encircles said valve body,
   said sewing ring including
      (a) tubular fabric sleeve means surrounding said valve body,
      (b) split sleeve means surrounding a section of said fabric sleeve means having two free ends and having second interconnecting means that interengages with said first interconnecting means when installed in surrounding relationship about said valve body and said fabric sleeve means and that when so interengaged prevents relative upstream-downstream movement therebetween, and
      (c) rigid circular continuous locking means fitted in encircling orientation about said split sleeve means in frictional engagement therewith so as to lock said fabric sleeve means between said first and second interconnecting means in frictional engagement between said valve body exterior surface and said split sleeve means and prevent disengagement of said fabric sleeve, said engagement between said rigid locking means and said split sleeve means being such that a gap remains between said free ends thereof and
   said tubular fabric sleeve means being manipulated so as to form at least a portion of sewing cuff means for suturing said prosthesis to tissue associated with a human heart.

18. The prosthesis according to claim 17 wherein said first interconnecting means comprises groove means in an otherwise generally cylindrical exterior surface of said valve body, wherein said second interconnecting means comprises interior projection means extending radially inward from an otherwise cylindrical interior surface of said split sleeve means, which interior projection means is proportioned to be received in and substantially fill said groove means and wherein said interior surface of said split sleeve means is proportioned to lie in juxtaposition with said exterior surface of said valve body.

* * * * *